US00PP13425P2

(12) United States Plant Patent
Olesen et al.

(10) Patent No.: US PP13,425 P2
(45) Date of Patent: Dec. 31, 2002

(54) MINIATURE ROSE VARIETY 'POULGILDO'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 48 days.

(21) Appl. No.: 09/677,573

(22) Filed: Sep. 27, 2000

(51) Int. Cl.[7] ..... A01H 5/00

(52) U.S. Cl. ..... Plt./118

(58) Field of Search ..... Plt./118, 125

(56) References Cited

PUBLICATIONS

US PP11,673, 12/2000, Olesen et al. (withdrawn)*
UPOV–ROM, 2001/04, Plant Variety Database, GTI Jouve Retrieval Software, citation for 'POULgildo'.*
Community Plant Variety Office. "Certificate on the Grant of Community Plant Variety Rights" Jun. 19, 2000. 6 pages. EU.

* cited by examiner

*Primary Examiner*—Howard J. Locker

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and 'POULjol' (non-patented). The two parents were crossed and the resulting seeds were planted in a controlled environment. The new variety is named 'POULgildo'.

The new rose may be distinguished from its seed parent, an unnamed seedling, by the following combination of characteristics:

1. The unnamed seed parent is yellow with pink intonations. 'POULgildo' has no pink intonations.

The new variety may be distinguished from its pollen parent, 'POULjol' created by the same inventors, by the following combination of characteristics:

1. 'POULjol' is a bright red rose, where 'POULgildo' is yellow.
2. 'POULjol' is taller and more vigorous in growth than 'POULgildo'.
3. 'POULjol' has a habit to be grown in a 10.5 cm pot, where 'POULgildo' has habit and size to be grown in a 6 cm pot.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The combination of qualities of this variety represents significant improvement over previously available commercial cultivars of this type and distinguishes 'POULgildo' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark in May of 1995.

'POULgildo' was selected by the inventors as a single plant from the progeny of the hybridization in Fredensborg, Denmark, in May of 1996. Asexual reproduction of 'POULgildo' by cuttings and traditional budding was first done by L. Pernille and Mogens N. Olesen in Fredensborg, Denmark in August, 1996. This initial and other subsequent propagations conducted in controlled environments have demonstrated that the characteristics of 'POULgildo' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULgildo'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Two stems, one bare, one with foliage.
6. Leaves.

DETAILED DESCRIPTION OF THE VARIETY

The following is a description of 'POULgildo', as observed in its growth on Half Moon Bay, Calif. Color references are made using The Royal Horticultural Society (London, England) Colour Chart, 1995, except where common terms of color are used.

For a comparison, several physical characteristics of the rose variety 'POULmoon', a miniature rose variety from the same inventors described and illustrated in U.S. Plant Pat. No. 11,673, dated Dec. 12, 2000 are compared to 'POULgildo' in Chart 1.

CHART 1

| | 'POULgildo' | 'POULmoon' |
|---|---|---|
| Petal color, upper surface | Yellow Group 4C. | Yellow Group 4C and Yellow Group 6C. |
| Petal color, lower surface. | Yellow Group 4B. | Yellow Group 4C and Yellow Group 6D. |
| Petalage | 35 to 38 petals, under normal conditions. | 35 to 40 petals, under normal conditions. |

Parents: Unnamed seedling×'POULjol'.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 23 mm–26 mm in length from base of receptacle to end of bud.
*Bud form.*—Short, globular,
*Bud color.*—As sepals unfold, Yellow Group 4A; Yellow Group 4A at ¼ opening.
*Sepals.*—Yellow-Green Group 144A. Weak foliaceous appendages on one to two of the five sepals. Surfaces of sepals moderately pubescent. Stipitate glands are present on edges of sepals.
*Receptacle.*—Surface: Smooth. Shape: Funnel-shaped. Size: 5 mm (h)×4 mm (w). Color: Yellow-Green Group 144A–B.
*Peduncle.*—Surface: Moderately abundant stipitate glands present. Length: 8 to 15 mm average length. Color: Yellow-Green Group 144 B–C.
*Borne.*—Generally with one bud per flowering stem.
Flower bloom:
*Fragrance.*—None.
*Duration.*—As a pot plant, flowers last from 7 to 8 days. As a cut flower 4 to 5 days.
*Size.*—Medium for a 6 cm pot rose. Average flower diameter 35 mm when open.
*Form.*—Shape of flower when viewed from the side: Upon opening, upper part: Cupped. Upon opening, lower part: Convex. Open flower, upper part: Flattened convex. Open flower, lower part: Flattened convex.
*Petalage.*—Average range: 35 to 38 petals under normal conditions with 5 to 7 petaloids.
Color:
*Upon opening, petals.*—Outermost petals: Upper Surface: Yellow Group 4C. Reverse Side: Yellow Group 4C. Innermost petals: Upper Surface: Yellow Group 4B. Reverse Side: Yellow Group 4B.
*Upon opening, basal petal spots.*—Outermost petals: Inner Side: Yellow Group 7 B–C. Outer Side: Yellow Group 7 B–C Innermost petals: Outer Side: Yellow Group 7 B–C. Inner Side: Yellow Group 7 B–C.
*After opening, petals.*—Outermost petals: Upper Surface: Yellow Group 4C. Reverse Side: Yellow Group 4C. Innermost petals: Upper Surface: Yellow Group 4B. Reverse Side: Yellow Group 4B.
*After opening, basal petal spots.*—Outermost petals: Inner Side: Yellow Group 7B–C. Innermost petals: Outer Side: Yellow Group 7A–B. Inner Side: Yellow Group 7A–B.
General tonality: On open flower Yellow Group 4C. No change in the general tonality at the end of the 7th day. Afterwards, general tonality is Yellow Group 4 C–D.
Petals:
*Petal reflex.*—Outer petals are double reflex. Inner petals are only somewhat reflexed.
*Petal edge.*—Emarginate.
*Shape.*—Ovate.
*Petaloids.*—Present; from 5 to 7 under normal conditions.
*Thickness.*—Average.
*Arrangement.*—Imbricated.
Reproductive organs:
*Pollen.*—Color: Yellow-Orange Group 21A–B. Abundance: Average.
*Anthers.*—Size: Medium. Color: Green-White Group 157A. Abundance: Average.
*Filaments.*—Color: Yellow-Green Group 154B.
*Stigmas.*—Slightly superior relative to anthers. Color: Green-White Group 157A.
*Styles.*—Color: Green-White Group 157A.

PLANT

Plant growth: Vigorous, compact. When grown in a 6 cm pot, as is typical in production of the variety, the average height of the plant itself is 9 to 11 cm and the average width is 8 to 11 cm.
Stems:
*Color.*—Young wood: Yellow-Green Group 144A–B. Older wood: Yellow-Green Group 144A–B.
*Prickles.*—Incidence: Very few. Size: Average length: 1 mm–2 mm. Color: Greyed-Yellow Group 160D. Shape: Linear.
*Surface.*—Young wood: Smooth. Older wood: Smooth.
*Plant foliage:* Normal number of leaflets on leaves in middle of the stem: 5 leaflets.
*Leaf size.*—20 mm (l)×10 mm (w).
*Quantity.*—Abundant.
*Color.*—Upper Leaf Surface: Green Group 137A. Lower Leaf Surface: Green Group 138B. Juvenile foliage: Upper surface is Green Group 138A. Lower surface is Green Group 138B.
Plant leaves and leaflets:
*Stipules.*—Size: 6 mm–9 mm. Color: Yellow-Green Group 144B. Stipitate Glands: Present on edges of stipule.
*Petiole.*—Length: 5 mm–10 mm. Color: Yellow-Green Group 144B. Underneath: Yellow-Green Group 144B. Moderate amount of stipitate glands observed. Margins: Moderate amount of stipitate glands observed.
*Rachis.*—Color: Yellow-Green Group 144B. Underneath: Yellow-Green Group 144B. Moderate amount of stipitate glands observed. Margins: Moderate amount of stipitate glands observed.
*Leaflet.*—Edge: Serrated. Shape: Ovate. Glossiness: Somewhat glossy.

Disease resistance: Average resistance to mildew, black spot, and Botrytis under normal growing conditions in Half Moon Bay, Calif.

We claim:

1. A new and distinct variety of rose plant of the miniature class, substantially as herein illustrated and described as a distinct and novel rose variety due to its abundant, yellow flowers, vigorous and compact growth, year round flowering under glasshouse conditions, suitability for production from softwood cuttings in pots, and durable flowers and foliage which make the variety suitable for distribution in the floral industry.

* * * * *

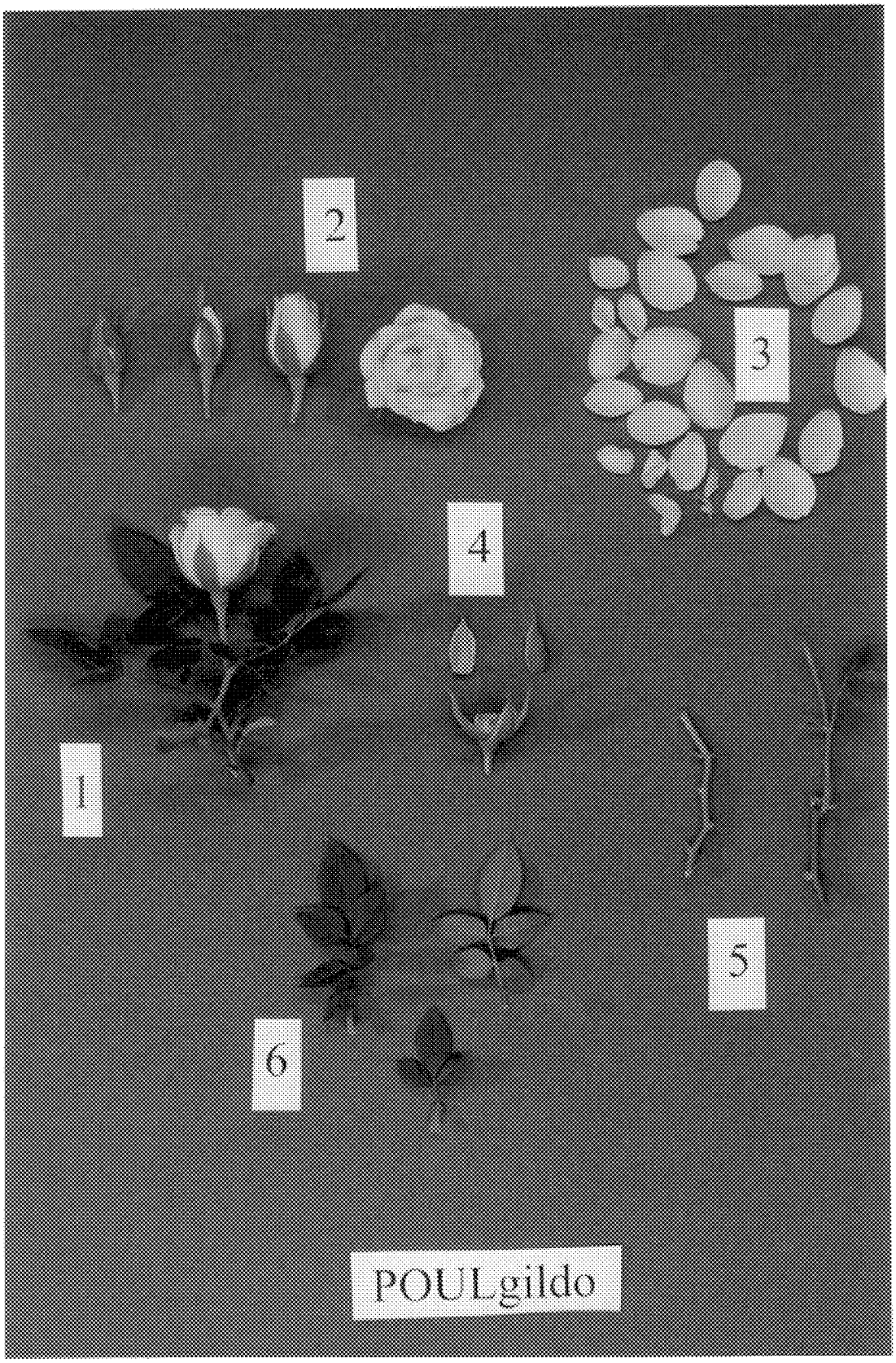
2
3
4
1
5
6
POULgildo